(12) United States Patent
Okazaki

(10) Patent No.: US 6,228,251 B1
(45) Date of Patent: May 8, 2001

(54) ELECTROLYTIC WATER PRODUCING APPARATUS AND CLEANING METHOD FOR THE SAME

(76) Inventor: Yoshiya Okazaki, 2-22, Nishi 1-chome, Kamifukuoka-shi (JP)

( * ) Notice: Subject to any disclaimer, the term of this patent is extended or adjusted under 35 U.S.C. 154(b) by 0 days.

(21) Appl. No.: 09/257,375

(22) Filed: Feb. 25, 1999

(30) Foreign Application Priority Data

Feb. 25, 1998 (JP) ................................................. 10-043792

(51) Int. Cl.$^7$ ...................................................... C02F 1/461

(52) U.S. Cl. ........................ 205/701; 205/746; 205/747; 205/751; 204/263; 204/264

(58) Field of Search ................................... 205/701, 746, 205/747, 751; 204/263, 264

(56) References Cited

U.S. PATENT DOCUMENTS 5,944,978 * 8/1999 Okazaki ............................... 205/746

* cited by examiner

*Primary Examiner*—Arun S. Phasge
(74) *Attorney, Agent, or Firm*—Jacobson, Price, Holman & Stern, PLLC

(57) ABSTRACT

Acid water containing hypochlorous acid is produced by an anode chamber of an electrolytic chamber, and alkali water is produced by a cathode chamber. The acid water is reserved in a reservoir tank and is returned into the anode chamber by actuating a return pump. The acid water returned into the anode chamber is subjected to further electrolysis, and fed in the cathode chamber through a first water supply line, an interconnection means and a second water supply line, so as to sterilize the interiors of the first water supply line, the interconnection and the second water supply line.

7 Claims, 3 Drawing Sheets

ELECTROLYTIC WATER PRODUCING APPARATUS AND CLEANING METHOD FOR THE SAME

TECHNICAL FIELD

The present invention relates to an electrolytic water producing apparatus comprising an electrolytic cell including an anode chamber and a cathode chamber, for producing alkali water and acid water, and a cleaning method for the electrolytic water producing apparatus, more specifically to an electrolytic water producing apparatus and a cleaning method for the electrolytic water producing apparatus which can effectively sterilize the anode chamber of the electrolytic cell.

BACKGROUND ART

Electrolytic water producing apparatuses each comprising an electrolytic cell including an anode chamber having an anode and a cathode chamber having a cathode have been conventionally known. In such electrolytic water producing apparatuses usual water is fed into the electrolytic cell to be made into alkali water and acid water in the electrolytic cell.

Generally calcium sticks to the cathode in the cathode chamber of the electrolytic cell as time passes, and the calcium is removed by changing over polarities of the anode and the cathode in the electrolytic cell (polarity reversion of the electrodes).

Of the alkali water and the acid water produced by the electrolytic water producing apparatuses, in some cases the former is used, the latter being drained, and in other cases the former is drained, the latter being used. In both cases, the cathode chamber is polluted with calcium. The use of the cathode chamber and the piping often increase bacteria, and the cathode chamber and the piping must be periodically sterilized and cleaned.

SUMMARY OF THE INVENTION

In consideration of these points the invention of the present application has been made. An object of the present invention is to provide an electrolytic water producing apparatus and a cleaning method therefore which can sterilize and clean the cathode chamber for producing alkali water, and the piping.

To this end, the electrolytic water producing apparatus according to the present invention comprises an electrolytic cell including an anode chamber having an anode, for producing acid water, and a cathode chamber having a cathode, for producing alkali water; an electric power source for applying a voltage between the anode and the cathode; a reservoir disposed on the side of an exit of the anode chamber of the electrolytic, for reserving the acid water; a discharge line disposed on the side of an exit of the cathode chamber of the electrolytic cell, for discharging the alkali water; a return mechanism for returning the acid water in the reservoir to the anode chamber; a first water supply line disposed on the side of an entrance of the anode chamber; a second water supply line disposed on the side of an entrance of the cathode chamber; and an interconnection means for interconnecting the first water feed line and the second water feed line.

The cleaning method for the electrolytic water producing apparatus comprises the steps of actuating the return mechanism to return the acid water in the reservoir to the anode chamber, feeding the acid water to the cathode chamber via the first water supply line, the interconnection means and the second water supply line, and then feeding the acid water outside from the cathode chamber; and applying a voltage between the anode and the cathode, so that the interior of the cathode chamber is sterilized by a high concentration of hypochlorous acid or hypochlorous acid soda.

According to the present invention, acid water in the reservoir tank is returned to the anode chamber by actuating the return mechanism, and a voltage is applied between the anode and the cathode, whereby a high concentration of hypochlorous acid or hypochlorous acid soda can be produced in the anode chamber. The high concentration of hypochlorous acid or hypochlorous acid soda is fed into the cathode chamber through the first feed line, the interconnection means and the second water feed line, sterilizing the interiors of the first water supply line, the interconnection means, the second water supply line and the cathode chamber, and is discharged outside through the discharge line, sterilizing the interior thereof.

BEST MODES FOR PRACTICING THE PRESENT INVENTION

Figure 1:
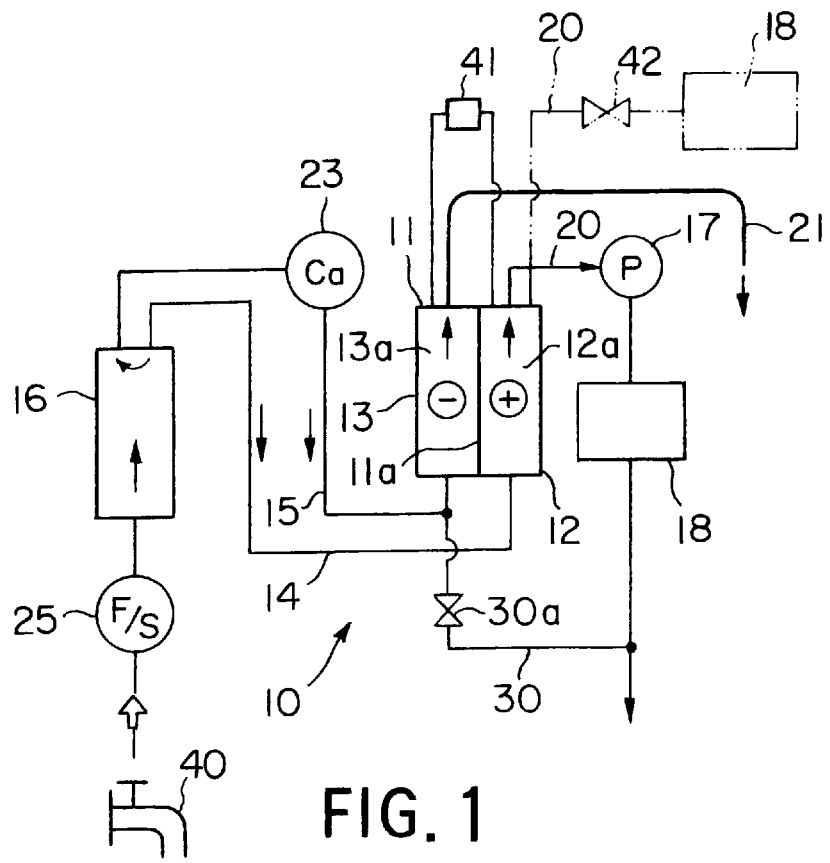
FIG. 1 is a view of the electrolytic water producing apparatus according to a first embodiment of the present invention in the normal operation.

The electrolytic water producing apparatus according to an embodiment of the present invention and the cleaning method for the same will be explained with reference to the drawings attached hereto. FIGS. 1 to 4 show the electrolytic water producing apparatus according to the embodiment and the cleaning method therefore.

With reference to FIGS. 1 to 4, an electrolytic water producing apparatus 10 for producing alkali water and acid water, comprises an electrolytic cell 11 including an anode 12 and a cathode 13 whose polarities are reversed therebetween. The interior of the electrolytic cell 11 is divided by a partition diaphragm 11a into an anode chamber 12a with the anode 12 and a cathode chamber 13a with the cathode 13. Acid water is produced in the anode chamber 12a, and alkali water is produced in the cathode chamber 13a.

A reservoir tank 18 is connected to the side of an exit of the anode chamber 12a through a feed line 20, and a feed line 21 is connected to the side of an exit of the cathode chamber 13a through a discharge line 21. A return pump (return mechanism) 17 for returning, in operation, the acid water in the reservoir tank 18 to the anode chamber 12a is disposed in the feed line 20 between the anode chamber 12a and the reservoir tank 18.

A first water supply line 14 is connected to the side of an entrance of the anode chamber 12a, and a second water supply line 15 is connected to the side of an entrance of the cathode chamber 13a. The first and the second water supply lines 14, 15 are connected to each other by an interconnection means 16. A flow sensor 25 which detects whether or not water is being fed into the electrolytic cell 11 from a water supply source 40 is disposed in the upstream of the interconnection means 16. Liquid chemical feed means 23 for feeding calcium into the water is disposed in the second water supply line 15.

A drain line 30 is connected to the cathode chamber 13a and the reservoir tank 18, and a drain valve 30a is provided in the drain line 30 on the side of the cathode chamber 13a.

Then, the operation of the present embodiment having such constitution will be explained.

In a normal operation, as shown in FIG. 1, water is supplied from the water supply source 40 into the anode chamber 12a and the cathode chamber 13a of the electrolytic cell 11 through the first water supply line 14 and the second water supply line 15. On the way, calcium is fed from the liquid chemical feed means 23 into the water in the second water supply line 15.

In the electrolytic cell 11, a required voltage and current are applied from an electric power source 41 to the anode 12 and the cathode 13. Alkali water and acid water (hypochlorous acid soda) are produced from the calcium-content water.

The acid water in the anode chamber 12a is fed from the return pump 17 into the reservoir tank 18 through the feed line 20 to be stored in the reservoir tank 18. On the other hand, the alkali water in the cathode chamber 13a is discharged outside for use. During this time, the drain valve 30a of the drain line 30 is closed.

As the operation is continuously carried out in the electrolytic cell 11, the calcium sticks to the cathode 13 in the electrolytic cell 11 and pollutes the cathode 13, then entirely polluting the interior of the cathode chamber 13a. The interior of the cathode chamber 13a must be sterilized and cleaned.

Figure 2:
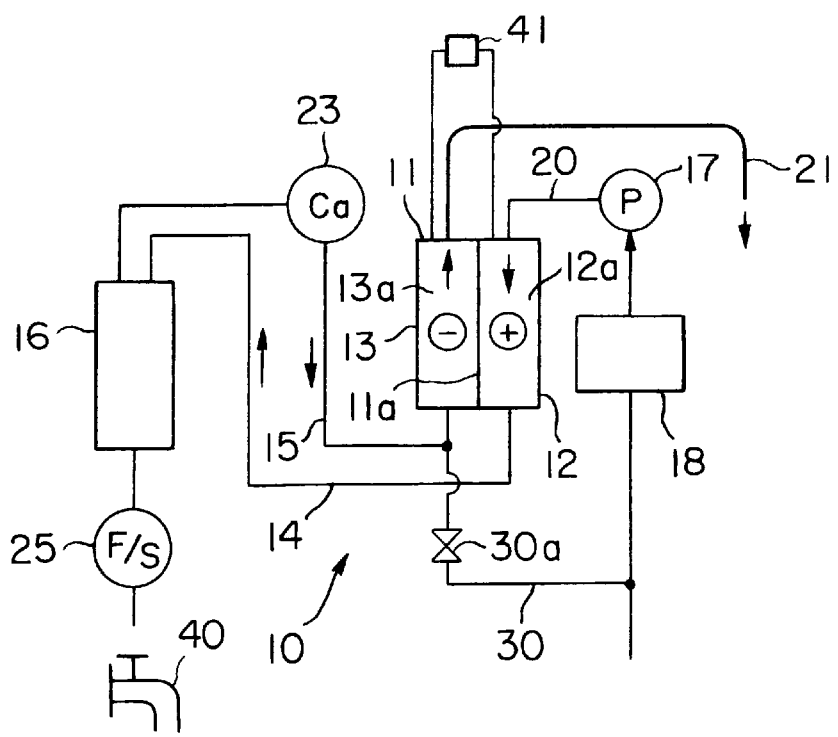
FIG. 2 is a view of the electrolytic water producing apparatus according to the first embodiment of the present invention in the cleaning operation.

Then, the cleaning operation shown in FIG. 2 performed. First the water supply from the water supply source 40 is stopped, and the return pump 17 is actuated.

At this time, the acid water in the reservoir tank 18 is returned into the anode chamber 12a. Then, a voltage and current are applied from the electric power source 41 to the anode 12 and the cathode 13 to increase in the anode chamber 12a a concentration of hypochlorous acid or hypochlorous acid soda in the acid water. Then, the acid water in the anode chamber 12a is fed into the cathode chamber 13a through the first water supply line 14, the interconnection means 16 and the second water supply line 15. The acid water having a hypochlorous acid or hypochlorous acid soda concentration thus increased is fed into the cathode chamber 13a, whereby the acid water of a high concentration can sterilize without failure the interior of the first water supply line 14, the interconnection means 16, the second water supply line 15 and the cathode chamber 13a.

The acid water which has sterilized the interior of the cathode chamber 13a, passes through the discharge line 21, and then is discharged outside so as to sterilize the interior of the discharge line 21.

Figure 3:
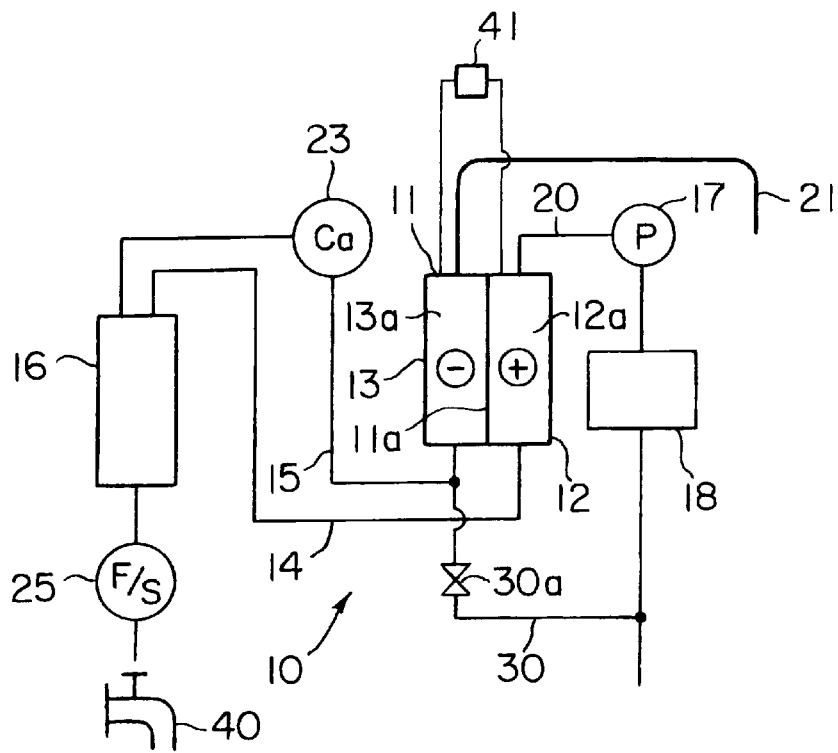
FIG. 3 is a view of the electrolytic water producing apparatus according to the first embodiment of the present invention in the polarity reversing operation.

Next, as shown in FIG. 3, with the return pump 17 stopped, the anode chamber 13a and the cathode chamber 12a are filled with water. Then, a voltage and a current under reversed polarities (polarity reversion) which are different from those for the normal operation are applied to the anode 12 and the cathode 13. When the voltage and the current under the polarity reversion are applied to the anode 12 and the cathode 13, solution of the calcium sticking to the cathode 13 and the partition diaphragm 11a is accelerated. A period of time in which the voltage and the current under the polarity reversion is preferably about 1 minute.

When the period of time in which the voltage and the current are applied under the polarity reversion is thus about 1 minute, loads exerted to the anode 12 and the cathode 13 can be reduced, and the anode 12 and the cathode 13 can last longer.

Figure 4:
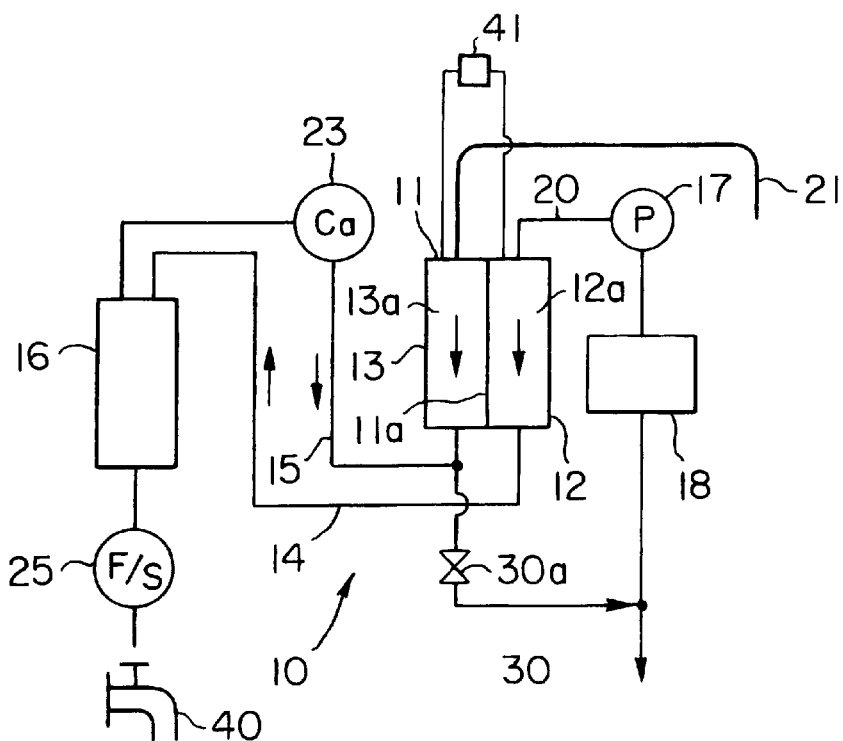
FIG. 4 is a view of the electrolytic water producing apparatus according to the first embodiment of the present invention in the draining operation.

Next, as shown in FIG. 4, the drain valve 30a is opened, and the water in the electrolytic cell is drained through the drain line 30. The water in the electrolytic cell 11 is thus drained.

Then, another embodiment of the present invention will be explained with reference to FIGS. 5 and 6.

Figure 5:
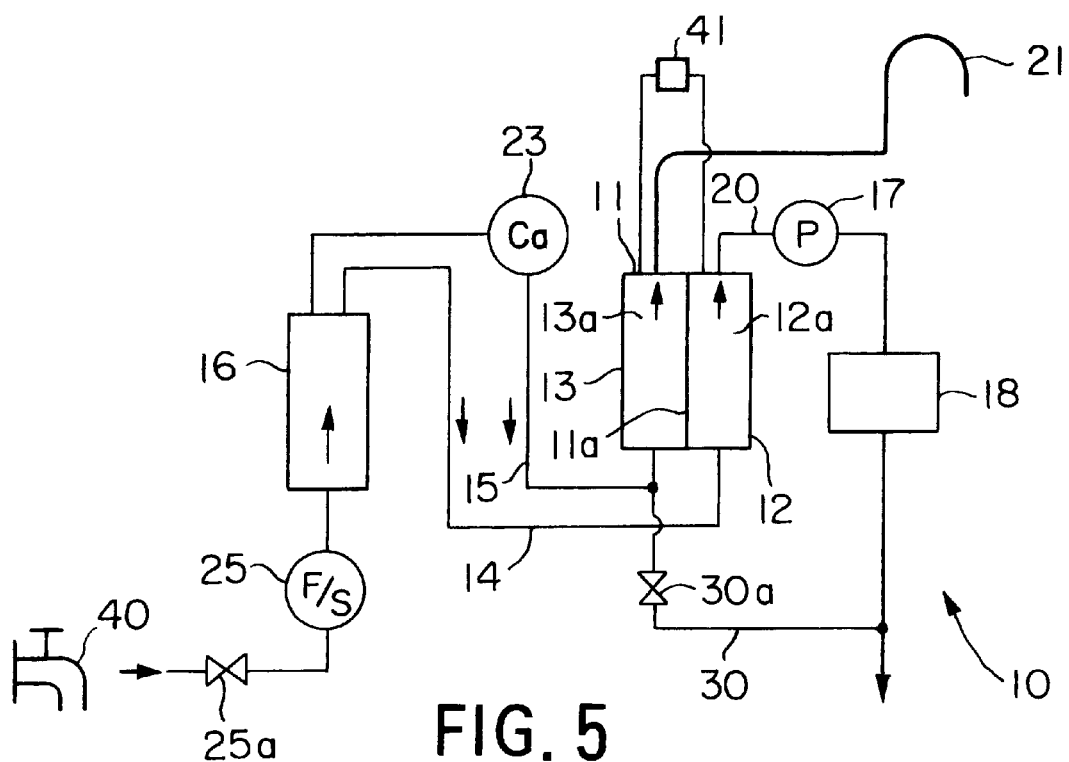
FIG. 5 is a view of the electrolytic water producing apparatus according to a second embodiment of the present invention in the normal operation.
Figure 6:
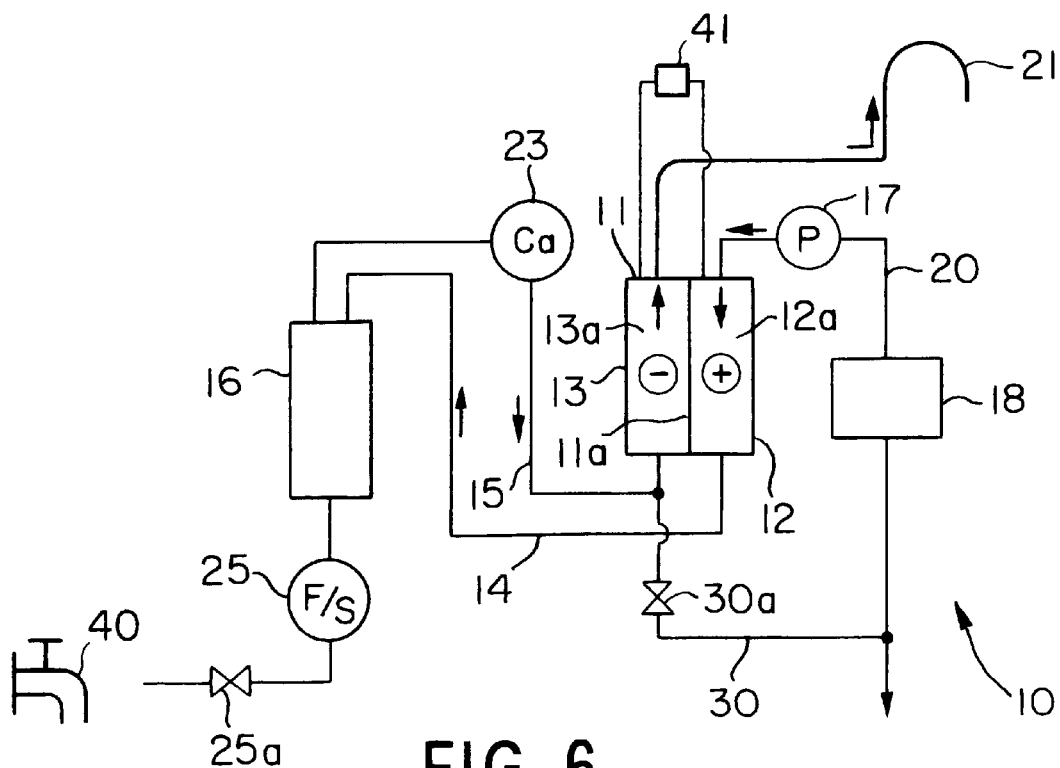
FIG. 6 is a view of the electrolytic water producing apparatus according to the second embodiment of the present invention in the cleaning operation.

The embodiment shown in FIGS. 5 and 6 includes a switch valve 25a disposed upstream of the flow sensor 25.

In a normal operation, as shown in FIG. 5, the switch valve 25a is opened to feed water which has passed through the flow sensor 25, into the electrolytic cell 11 through the interconnection means 16, the first water supply line 14 and the second water supply line 15. Then, acid water is produced in the anode chamber 12a of the electrolytic cell 11, and alkali water is produced in the anode chamber 13a. The acid water produced in the anode chamber 12a is reserved in the reservoir tank 18 via the return pump 17, and the alkali water produced in the cathode chamber 13a is discharged through the discharge line 21.

In a cleaning operation, as shown in FIG. 6, the switch valve 25a is closed, and the return pump 17 is actuated to cause the acid water in the reservoir tank 18 to flow into the anode chamber 12a.

During this time, a voltage and a current are applied between the anode 12 and the cathode 13, and a concentration of hypochlorous acid or hypochlorous acid soda in the acid water in the anode chamber 12a is increased. Then, the acid water is fed from the anode chamber 12a into the cathode chamber 13a through the first water supply line 14, the interconnection means 16 and the second water supply line 15, sterilizing the interiors of the first water supply line 14, the interconnection means 16, the second water supply line 15 and the cathode chamber 13a, and then is discharged outside.

In this case, the return pump 17 is intermittently operated, so that the acid water can be temporarily reserved in the anode chamber 12a. Accordingly, a concentration of hypochlorous acid or hypochlorous acid soda can be increased. As acid water of high concentration can be thus fed into the cathode chamber 13a, the effect of sterilizing the interiors of the first water supply line 14, the interconnection means 16, the second water supply line 15, the cathode chamber 13a and the discharge line 21, can be increased.

Then, with the switch valve 25a opened, water is automatically supplied into the electrolytic cell 11, and the above-described operation is repeated to store acid water in the reservoir tank 18. Then, with the switch valve 25a closed, the acid water in the reservoir tank 18 is returned by the pump 17 from the anode chamber 12a to the cathode chamber 13a to sterilize the interior of the cathode chamber 13a. Such sterilizing operation is repeated, whereby the interiors of the cathode chamber 13a, and the water supply lines 14, 15 can be effectively sterilized.

In the above-described respective embodiments, the return mechanism for returning the acid water into the reservoir tank 18 is unessentially the return pump 17, and it is possible that, as shown in FIG. 1, the reservoir tank 18 is positioned above the electrolytic cell 11 so that the acid water in the reservoir tank 18 is returned into the anode chamber 12a of the electrolytic cell 11 by a head of the acid water in the reservoir tank 18. In this case, a switch valve 42 is disposed in the feed line 20, whereby a return amount of the acid water and a return timing can be adjusted.

As described above, according to the present invention, a high concentration of hypochlorous acid or hypochlorous acid soda is fed into the first water supply line, the interconnection, the second water supply line and the cathode chamber, whereby the interiors of the first water supply line, the interconnection means, the second water supply lie and the cathode chamber can be sterilized by the high concentration of hypochlorous acid or hypochlorous acid soda. Then, the hypochlorous acid or hypochlorous acid soda is discharged outside, sterilizing the interior of the discharge line.

What is claimed is:

1. An electrolytic water producing apparatus comprising:
   an electrolytic cell including an anode chamber having an anode, for producing acid water, and a cathode chamber having a cathode, for producing alkali water;
   an electric power source for applying a voltage between the anode and the cathode;
   a reservoir disposed on the side of the side of an exit of the anode chamber of the electrolytic, for reserving the acid water;
   a discharge line disposed on the side of an exit of the cathode chamber of the electrolytic cell, for discharging the alkali water;
   a return mechanism for returning the acid water in the reservoir to the anode chamber;
   a first water supply line disposed on the side of an entrance of the anode chamber;
   a second water supply line disposed on the side of an entrance of the cathode chamber; and
   an interconnection means for interconnecting the first water feed line and the second water feed line.

2. The electrolytic water producing apparatus according to claim 1, wherein
   a feed line is disposed on the side of the exit of the anode chamber, and the return mechanism is disposed in the feed line.

3. The electrolytic water producing apparatus according to claim 2, wherein
   the reservoir is positioned above the electrolytic cell, and the return mechanism comprises a switch valve disposed in the feed line.

4. The electrolytic water producing apparatus according to claim 2, wherein
   the return mechanism comprises a return pump disposed in the feed line.

5. The electrolytic water producing apparatus according to claim 1, wherein
   a drain line is disposed in the electrolytic cell.

6. A cleaning method for an electrolytic water producing apparatus comprising an anode chamber including an anode, for producing acid water and a cathode chamber including a cathode, for producing alkali water, an electric power source for applying a voltage between the anode and the cathode, a reservoir disposed on the side of the anode chamber of the electrolytic cell, for reserving the acid water, a discharge line disposed on the side of an exit of the cathode chamber of the electrolytic cell, for discharging the alkali water, a discharge line disposed on the side of an exit of the cathode chamber of the electrolytic cell, for discharging the alkali water, a return mechanism for returning the acid water in the reservoir to the anode chamber, a first water supply line disposed on the side of an entrance of the anode chamber, a second water feed line disposed on the side of an entrance of the cathode chamber, and interconnection means for interconnecting the first water supply line and the second water supply line, the method comprising the steps of:
   actuating the return mechanism to return the acid water in the reservoir to the anode chamber, feeding the acid water to the cathode chamber via the first water supply line, the interconnection means and the second water supply line, and then discharging the acid water outside from the cathode chamber; and
   applying a voltage between the anode and the cathode, so that the interior of the cathode chamber is sterilized by a high concentration of hypochlorous acid or hypochlorous acid soda.

7. The method for cleaning an electrolytic water producing device according to claim 6, wherein
   the step of actuating the return mechanism is intermittently performed to thereby increase the concentration of hypochlorous acid or hypochlorous acid soda in the anode chamber.

* * * * *